United States Patent
Shyur et al.

(10) Patent No.: US 7,037,696 B1
(45) Date of Patent: May 2, 2006

(54) TRUNCATED FORM OF FIBROBACTER SUCCINOGENES 1,3-1, 4-β-D-GLUCANASE WITH IMPROVED ENZYMATIC ACTIVITY AND THERMO-TOLERANCE

(75) Inventors: Lie-Fen Shyur, Taipei (TW); Jui-Lin Chen, Taipei (TW); Ning-Sun Yang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/654,652

(22) Filed: Sep. 5, 2000

(51) Int. Cl.
*C12N 9/02* (2006.01)

(52) U.S. Cl. .......... 435/189; 435/440; 435/25; 435/252.3; 435/320.1; 435/69.1; 536/23.2; 536/23.7

(58) Field of Classification Search .......... 435/201, 435/440, 252.3, 195, 189, 25, 69.1, 71.1, 435/320.1; 536/23.2, 23.7; 530/350
See application file for complete search history.

(56) References Cited

U.S. PATENT DOCUMENTS 6,103,511 A * 8/2000 Li et al. ............... 435/209

OTHER PUBLICATIONS

Teather et al., DNA Sequence of a Fibrobacter succinogenes Mixed-Linkage -Glucanase (1,3-1,4- -D-Glucan 4-Glucanohydrolase) Gene, *Journal of Bacteriology*, pp. 3837-3841 (1990).

Irvin et al., "Cloning and Expression of a Bacteroides succinogenes Mixed-Linked -Glucanase (1,3-1,4- -D-Glucan 4-Glucanohydrolase) Gene in *Escherichia coli*", *Applied and Environmental Microbiology*, pp. 2672-2676 (1988).

Erfle et al., "Purifcation and properties of a 1,3-1,4- -D-glucanase (lichenase, 1,3-1,4- -D-glucan 4-glucanohydrolase, EC 3.2.1.73) from Bacteroides succinogenes cloned in *Escherichia coli*", *Biochem J.* pp. 833-841 (1988).

* cited by examiner

Primary Examiner—Ponnathapu Achutamurthy
Assistant Examiner—Yong D. Pak
(74) Attorney, Agent, or Firm—Cohen, Pontani, Lieberman & Pavane (57) ABSTRACT

A truncated glucanase with an improved thermal stability and a higher specific enzymatic activity than the wild-type enzyme. The truncated glucanase is obtained by removing a number of amino acid residues from the C-terminal of the wild-type 1,3-1,4-β-D-glucanase of *Fibrobacter succinogenes*. The removal of the C-terminal amino acid residues can be conducted at the genetic level by modifying the gene encoding for the wild type enzyme using, for example, a PCR-based method. Or, it can also be conducted at the protein level by first producing the wild-type enzyme protein and then subjecting the wild-type protein to certain protease action to remove a portion of its C-terminal.

2 Claims, 7 Drawing Sheets

Fig. 1

Fig. 2  The amino acid sequence in Fig. 2 is SEQ ID NO: 1
The DNA sequence in Fig. 2 is SEQ ID NO: 4

```
ATGGTTAGCGCAAAGGATTTTAGCGGTGCCGAACTCTACACGTTAGAAGAAGTTCAGTAC
 M   V   S   A   K   D   F   S   G   A   E   L   Y   T   L   E   E   V   Q   Y     20

GGTAAGTTTGAAGCCCGTATGAAGATGGCAGCCGCATCGGGAACAGTCAGTTCCATGTTC
 G   K   F   E   A   R   M   K   M   A   A   A   S   G   T   V   S   S   M   F     40

CTCTACCAGAATGGTTCCGAAATCGCCGATGGAAGGCCCTGGGTAGAAGTGGATATTGAA
 L   Y   Q   N   G   S   E   I   A   D   G   R   P   W   V   E   V   D   I   E     60

GTTCTCGGCAAGAATCCGGGCAGTTTCCAGTCCAACATCATTACCGGTAAGGCCGGCGCA
 V   L   G   K   N   P   G   S   F   Q   S   N   I   I   T   G   K   A   G   A     80

CAAAAGACTAGCGAAAAGCACCATGCTGTTAGCCCCGCCGCCGATCAGGCTTTCCACACC
 Q   K   T   S   E   K   H   H   A   V   S   P   A   A   D   Q   A   F   H   T    100

TACGGTCTCGAATGGACTCCGAATTACGTCCGCTGGACTGTTGACGGTCAGGAAGTCCGC
 Y   G   L   E   W   T   P   N   Y   V   R   W   T   V   D   G   Q   E   V   R    120

AAGACGGAAGGTGGCCAGGTTTCCAACTTGACAGGTACACAGGGACTCCGTTTTAACCTT
 K   T   E   G   G   Q   V   S   N   L   T   G   T   Q   G   L   R   F   N   L    140

TGGTCGTCTGAGAGTGCGGCTTGGGTTGGCCAGTTCGATGAATCAAAGCTTCCGCTTTTC
 W   S   S   E   S   A   A   W   V   G   Q   F   D   E   S   K   L   P   L   F    160

CAGTTCATCAACTGGGTCAAGGTTTATAAGTATACGCCGGGCCAGGGCGAAGGCGGCAGC
 Q   F   I   N   W   V   K   V   Y   K   Y   T   P   G   Q   G   E   G   G   S    180

GACTTTACGCTTGACTGGACCGACAATTTTGACACGTTTGATGGCTCCCGCTGGGGCAAG
 D   F   T   L   D   W   T   .D   N   F   D   T   F   D   G   S   R   W   G   K    200

GGTGACTGGACATTTGACGGTAACCGTGTCGACCTCACCGACAAGAACATCTACTCCAGA
 G   D   W   T   F   D   G   N   R   V   D   L   T   D   K   N   I   Y   S   R    220

GATGGCATGTTGATCCTCGCCCTCACCCGCAAAGGTCAGGAAAGCTTCAACGGCCAGGTT
 D   G   M   L   I   L   A   L   T   R   K   G   Q   E   S   F   N   G   Q   V    240

CCGAGAGATGACGAACCTGCTCCG
 P   R   D   D   E   P   A                                                        248
```

Fig. 3 The amino acid sequence in Fig. 3 is SEQ ID NO: 2

The DNA sequence in Fig. 3 is SEQ ID NO: 5

```
ATGGTTAGCGCAAAGGATTTTAGCGGTGCCGAACTCTACACGTTAGAAGAAGTTCAGTAC
 M  V  S  A  K  D  F  S  G  A  E  L  Y  T  L  E  E  V  Q  Y   20

GGTAAGTTTGAAGCCCGTATGAAGATGGCAGCCGCATCGGGAACAGTCAGTTCCATGTTC
 G  K  F  E  A  R  M  K  M  A  A  A  S  G  T  V  S  S  M  F   40

CTCTACCAGAATGGTTCCGAAATCGCCGATGGAAGGCCCTGGGTAGAAGTGGATATTGAA
 L  Y  Q  N  G  S  E  I  A  D  G  R  P  W  V  E  V  D  I  E   60

GTTCTCGGCAAGAATCCGGGCAGTTTCCAGTCCAACATCATTACCGGTAAGGCCGGCGCA
 V  L  G  K  N  P  G  S  F  Q  S  N  I  I  T  G  K  A  G  A   80

CAAAAGACTAGCGAAAAGCACCATGCTGTTAGCCCCGCCGCCGATCAGGCTTTCCACACC
 Q  K  T  S  E  K  H  H  A  V  S  P  A  A  D  Q  A  F  H  T  100

TACGGTCTCGAATGGACTCCGAATTACGTCCGCTGGACTGTTGACGGTCAGGAAGTCCGC
 Y  G  L  E  W  T  P  N  Y  V  R  W  T  V  D  G  Q  E  V  R  120

AAGACGGAAGGTGGCCAGGTTTCCAACTTGACAGGTACACAGGGACTCCGTTTTAACCTT
 K  T  E  G  G  Q  V  S  N  L  T  G  T  Q  G  L  R  F  N  L  140

TGGTCGTCTGAGAGTGCGGCTTGGGTTGGCCAGTTCGATGAATCAAAGCTTCCGCTTTTC
 W  S  S  E  S  A  A  W  V  G  Q  F  D  E  S  K  L  P  L  F  160

CAGTTCATCAACTGGGTCAAGGTTTATAAGTATACGCCGGGCCAGGGCGAAGGCGGCAGC
 Q  F  I  N  W  V  K  V  Y  K  Y  T  P  G  Q  G  E  G  G  S  180

GACTTTACGCTTGACTGGACCGACAATTTTGACACGTTTGATGGCTCCCGCTGGGGCAAG
 D  F  T  L  D  W  T  D  N  F  D  T  F  D  G  S  R  W  G  K  200

GGTGACTGGACATTTGACGGTAACCGTGTCGACCTCACCGACAAGAACATCTACTCCAGA
 G  D  W  T  F  D  G  N  R  V  D  L  T  D  K  N  I  Y  S  R  220

GATGGCATGTTGATCCTCGCCCTCACCCGCAAAGGTCAGGAAAGCTTCAACGGCCAGGTT
 D  G  M  L  I  L  A  L  T  R  K  G  Q  E  S  F  N  G  Q  V  240

CCGAGAGATGACGAACCTGCTCCGAATTCGAGCTCCGTCGACAAGCTTGCGGCCGCACTC
 P  R  D  D  E  P  A  P  N  S  S  S  V  D  K  L  A  A  A  L  260

GAGCACCACCACCACCACCACTGA
 E  H  H  H  H  H  H  *                                        267
```

Fig. 4

Table 1. Comparison of kinetic properties of *F. succinogenes* and *B. subtilis* 1,3-1,4-β-D-glucanases

| Enzyme | Specific activity (U/mg) | $k_{cat}$ ($^{-1}$s) | Opt. Temperature (°C) | Opt. pH |
|---|---|---|---|---|
| Wild-type | 2065 ± 82 | 1296 ± 51 | 50 (at pH 6.0) | 6.0-8.0 |
| TG-Glucanase | 7980 ± 341 | 3695 ± 158 | 50 (at pH 6.0) | 6.0-8.0 |
| PCR-TF-Glucanase | 7833 ± 334 | 3911 ± 166 | 50 (at pH 6.0) | 6.0-8.0 |
| Lichanase (Megazyme) | 118[a] | 47.2[a] | 60 (at pH 6.5)[a] | 6.5-7.0[a] |
| | 82.6 ± 0.96 | 33.0 ± 0.38 | 55 (at pH 7.0) | |

The kinetics was performed with lichenan (6mg/mL) as substrate in 50 mM citrate buffer (pH 6.0) or in 50mM phosphate buffer (pH 7.0), and at optimum temperature as indicated.

[a]: Data was taken from *Megazyme* instruction brochure of lichenase. The kinetics was done with barley β-glucan (5mg/mL) as substrate.

Fig. 5

Table 3. Reactivation of PCR-TF-glucanase at 25 °C after heat treatment

| Heat treatment | Recovery time (min) | Relative activity (%) |
| --- | --- | --- |
| 90 °C, 10 min | 10 | 68 |
|  | 20 | 81 |
| 90 °C, 30 min | 10 | 61 |
|  | 20 | 67 |
| 100 °C, 10 min | 10 | 68 |
|  | 20 | 72 |
| 100 °C, 30 min | 10 | 55 |
|  | 20 | 56 |

Fig. 6 (part a)

The amino acid sequence in Fig. 6 is SEQ ID NO: 3
The DNA sequence in Fig. 6 is SEQ ID NO: 6

```
ATGAACATCAAGAAAACTGCAGTCAAGAGCGCTCTCGCCGTAGCAGCCGCAGCAGCAGCC
 M   N   I   K   K   T   A   V   K   S   A   L   A   V   A   A   A   A   A   A    20

CTCACCACCAATGTTAGCGCAAAGGATTTTAGCGGTGCCGAACTCTACACGTTAGAAGAA
 L   T   T   N   V   S   A   K   D   F   S   G   A   E   L   Y   T   L   E   E    40

GTTCAGTACGGTAAGTTTGAAGCCCGTATGAAGATGGCAGCCGCATCGGGAACAGTCAGT
 V   Q   Y   G   K   F   E   A   R   M   K   M   A   A   A   S   G   T   V   S    60

TCCATGTTCCTCTACCAGAATGGTTCCGAAATCGCCGATGGAAGGCCCTGGGTAGAAGTG
 S   M   F   L   Y   Q   N   G   S   E   I   A   D   G   R   P   W   V   E   V    80

GATATTGAAGTTCTCGGCAAGAATCCGGGCAGTTTCCAGTCCAACATCATTACCGGTAAG
 D   I   E   V   L   G   K   N   P   G   S   F   Q   S   N   I   I   T   G   K   100

GCCGGCGCACAAAAGACTAGCGAAAAGCACCATGCTGTTAGCCCCGCCGCCGATCAGGCT
 A   G   A   Q   K   T   S   E   K   H   H   A   V   S   P   A   A   D   Q   A   120

TTCCACACCTACGGTCTCGAATGGACTCCGAATTACGTCCGCTGGACTGTTGACGGTCAG
 F   H   T   Y   G   L   E   W   T   P   N   Y   V   R   W   T   V   D   G   Q   140

GAAGTCCGCAAGACGGAAGGTGGCCAGGTTTCCAACTTGACAGGTACACAGGGACTCCGT
 E   V   R   K   T   E   G   G   Q   V   S   N   L   T   G   T   Q   G   L   R   160

TTTAACCTTTGGTCGTCTGAGAGTGCGGCTTGGGTTGGCCAGTTCGATGAATCAAAGCTT
 F   N   L   W   S   S   E   S   A   A   W   V   G   Q   F   D   E   S   K   L   180

CCGCTTTTCCAGTTCATCAACTGGGTCAAGGTTTATAAGTATACGCCGGGCCAGGGCGAA
 P   L   F   Q   F   I   N   W   V   K   V   Y   K   Y   T   P   G   Q   G   E   200

GGCGGCAGCGACTTTACGCTTGACTGGACCGACAATTTTGACACGTTTGATGGCTCCCGC
 G   G   S   D   F   T   L   D   W   T   D   N   F   D   T   F   D   G   S   R   220

TGGGGCAAGGGTGACTGGACATTTGACGGTAACCGTGTCGACCTCACCGACAAGAACATC
 W   G   K   G   D   W   T   F   D   G   N   R   V   D   L   T   D   K   N   I   240

TACTCCAGAGATGGCATGTTGATCCTCGCCCTCACCCGCAAAGGTCAGGAAAGCTTCAAC
 Y   S   R   D   G   M   L   I   L   A   L   T   R   K   G   Q   E   S   F   N   260

GGCCAGGTTCCGAGAGATGACGAACCTGCTCCGCAATCTTCTAGCAGCGCTCCGGCATCT
 G   Q   V   P   R   D   D   E   P   A   P   Q   S   S   S   S   A   P   A   S   280

TCTAGCAGTGTTCCGGCAAGCTCCTCTAGCGTCCCTGCCTCCTCGAGCAGCGCATTTGTT
 S   S   S   V   P   A   S   S   S   S   V   P   A   S   S   S   S   A   F   V   300

CCGCCGAGCTCCTCGAGCGCCACAAACGCAATCCACGGAATGCGCACAACTCCGGCAGTT
```

Fig 6
(pmtb)

```
        P   P   S   S   S   S   A   T   N   A   I   H   G   M   R   T   T   P   A   V  320
GCAAAGGAACACCGCAATCTCGTGAACGCCAAGGGTGCCAAGGTGAACCCGAATGGCCAC
        A   K   E   H   R   N   L   V   N   A   K   G   A   K   V   N   P   N   G   H  340

AAGCGTTATCGCGTGAACTTTGAACACTAA
        K   R   Y   R   V   N   F   E   H   *                                          349
```

TRUNCATED FORM OF FIBROBACTER SUCCINOGENES 1,3-1, 4-β-D-GLUCANASE WITH IMPROVED ENZYMATIC ACTIVITY AND THERMO-TOLERANCE

BACKGROUND OF THE INVENTION

1. Field of the Invention

This invention relates to a truncated form of 1,3-1,4--D-Glucanase (lichenase, EC 3.2.1.73) with enhanced enzymatic activity and thermal tolerance.

2. Description of the Related Art 1,3-1,4-β-D-Glucanase is an endo-β-D-glucanase that can specifically hydrolyze 1,4-β-D-glucosidic bonds adjacent to 1,3-β-linkages in mix-linked β-glucans, yielding mainly cellobiosyltriose and cellotriosyltetraose. The enzyme has received much attention in both basic and applied research areas because of its enzymatic functions and importance in industrial applications. Supplementation of this fibrolytic enzyme in animal feed is one of the approaches for increasing the feed conversion efficiency and growth-rate of non-ruminal animals (Bedford et al., 1992; Selinger et al., 1996). This enzyme is also attractive for its application in the brewing industry. This enzyme has been used to substitute or supplement malt enzymes for reducing the industrial processing problem(s) caused by β-glucans from cell walls of the starchy seed endosperm, which include, for example, the reduced yield of extract, lowered rates of wort separation and beer filtration, formation of hazes and gelatinous precipitates in beer (Uhilg, 1998). However, the wide use of 1,3-1,4-β-D-glucanase as an industrial enzyme in general has a major drawback, that is, the limitation imposed by the thermal stability of the enzyme during industrial processes. For instance, the elevated temperatures employed in the malting process (50–70° C.) or the feed-pelleting and/or expansion processes (65–90° C.) may cause severe inactivation of the enzyme. Therefore, creation of heat-resistant enzymes would overcome the aforementioned problem. Moreover, an enzyme with high catalytic activity would be more desirable in industrial applications in terms of cost-effectiveness.

*Fibrobacter succinogenes* is a microorganism that plays a major role in plant fiber digestion in the rumen. From this organism, several enzymes related to the digestion of cellulose or hemicellulose polymers of plant cell wall have been isolated and studied (Selinger et al., 1996). One of the *Fibrobacter succinogenes* emzymes, 1,3-1,4-β-D-glucanase or Fsβ-glucanase, is isolated and characterized by Teather et al. (1988 & 1990). This enzyme consists of a protein sequence with circular permutation in which two highly conservative catalytic domains of the enzyme are in a reverse orientation, as compared to that of 1,3-1,4-β-D-glucanases from other sources (Teather & Erfle, 1990; Schimming et al., 1992; Heinemann & Hahn, 1995). Five repeated serine-rich regions are found in the C-terminal, which are nonhomologous relative to bacilli or other bacterial 1,3-1,4-β-D-glucanases.

One objective of the present invention is to provide a new form of glucanase having both enhanced enzymatic activity and improved thermal stability. This objective is achieved by truncating a wild-type 1,3-1,4-β-D-glucanase whereby producing a shortened form of the enzyme. This truncated form of glucanase, with significant enhancement both in the enzymatic activity and in the thermal stability, and the method for producing the truncated enzyme are hereby disclosed.

SUMMARY OF THE INVENTION

According to the present invention, both the enzymatic activity and the thermal stability of the *Fibrobacter succinogenes* glucanase enzyme can be greatly enhanced by removing a number of amino acid residues from its C-terminal. According to another aspect of the invention, the removal of the C-terminal portion of the enzyme can be achieved either by modification of the gene encoding for the enzyme prior to protein expression or by post-expression modification of the enzyme at the protein level. For example, in a preferred embodiment, pre-expression modification is carried out using a PCR-based gene truncation method, resulting in a truncation of the wild-type enzyme for glucanase. The truncated gene is then incorporated into an expression vector and expressed in *E. coli*, producing a truncated glucanase (hereinafter referred as "PCR-TF-glucanase") that is about 10 kDa smaller than the full-length wild-type enzyme. In another preferred embodiment, truncated glucanase can also be made by first expressing the wild-type enzyme and then incubating the wild type enzyme for a certain period of time and under certain conditions. The resulting truncated enzyme, with a molecular weight of approximately 27.72 kDa, is hereinafter referred to as "TF-glucanase".

Both truncated enzymes, i.e., TF-glucanase, which directly derived from the full-length protein, and PCR-TF-glucanase, which is expressed from a PCR-truncated gene, show an approximate 3.9-fold increase in the specific activity as compared to that of the full-length enzyme. The specific activity, measured with lichenan as the substrate, for the wild-type, TF-glucanase, and PCR-TF-glucanase enzymes is 2065, 7980, and 7833 μmol/min/mg, respectively. The specific activity, if measured with barley β-glucan as substrate, is 2600, 7682, and 7975 μmol/min/mg, repectively. For comparison, the specific activity of a hybrid 1,3-1,4-β-D-glucanase, H(A16-M), constructed from the *Bacillus macerans* and *Bacillus amyloliquefaciens* enzymes (Politz, et al., 1993), is reportedly 4,890 μmol/min/mg with lichenan as the substrate at 65° C. (Hahn et al., 1994). The $V_{max}$ value for a fungal 1,3-1,4-β-D-glucanase from *Orpinomzyces* strain PC-2 with lichenan and barley β-glucan as the substrate at pH 6.0 and 40° C. are 3,790 μmol/min/mg and 5,320 μmol/min/mg, respectively (Chen et al., 1997). A commercially available 1,3-1,4-β-D-glucanase (lichenase, Megazyme International Ireland Ltd.) produced from *Bacillus subtilis* has a specific activity of 118 U/mg. Therefore, the truncated enzymes of the present invention are 1.5-, 1.6- and 68-fold higher in specific activity than the *Orpinomyces* 1,3-1,4-β-D-glucanase, H(A16-M) 1,3-1,4-β-D-glucanase and the *Bacillus lichenase* (Megazyme). The PCR-TF-glucanase and TF-glucanase, to applicants' knowledge, is the most active 1,3-1,4-β-D-glucanase.

In addition to the enhanced specific activity, the truncated glucanse has an improved thermal stability. For example, TF-glucanase and PCR-TF-glucanase produced in preferred embodiments, can retain 80–85% of their original enzymatic activity after a 10 minute incubation at 90° C., whereas the full-length enzyme can retain only 30% of its original enzymatic activity after the same heat treatment. As a further comparison, the *Bacillus lichenase* from Megazyme company retains less than 10% of its activity under the same conditions. Under more severe conditions, such as being boiled for 10–30 minutes, PCR-TF-glucanase still retains 55–70% of its original activity.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, like reference characters denote similar elements throughout the several views.

DETAILED DESCRIPTION OF THE PRESENTLY PREFERRED EMBODIMENTS

EXAMPLE I

Enzyme Truncation at the DNA Level

Figure 1:
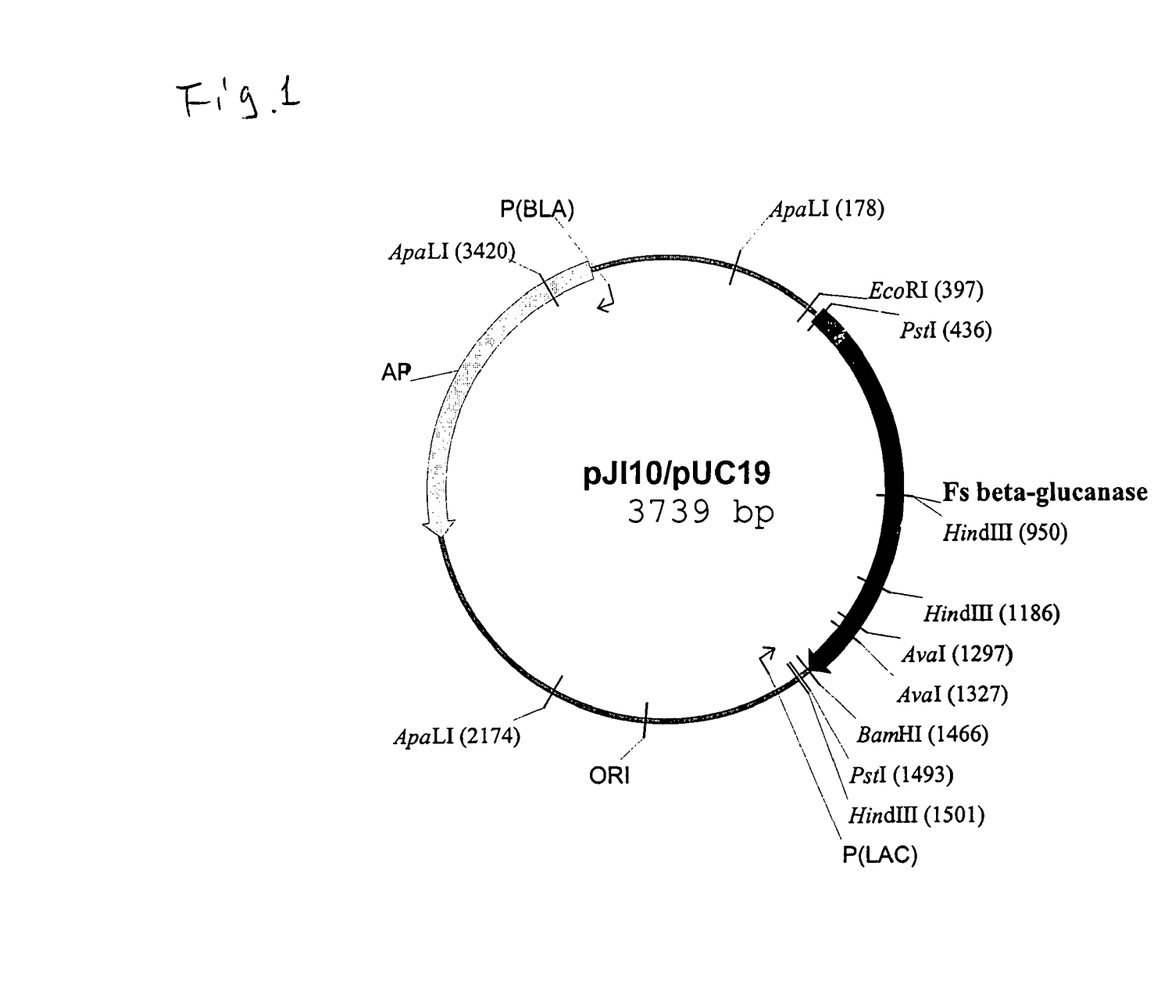
FIG. 1 is a genetic map of pJI10 plasmid deduced from the prior art references, which contains a full-length genetic code for 1,3-1,4-β-D-glucanase of *Fibrobacter succinogenes*.

Subcloning of Wild-type Glucanase Gene pJI10, a plasmid containing a wild-type gene of *Fibrobacter succinogenes* 1,3-1,4-β-D-glucanase (alse known as Fsβ-glucanase), can be used as a template for the purpose of subcloning the gene, although other DNA templates can also be satisfactorily used as long as they contain the desired glucanase gene. pJI10, whose genetic map is delineated in FIG. 1, is fully described in the prior art by Teather and Erfle in "Cloning and expression of a *Bacteriod succinogenes* mixed-linkage β-glucanase (1,3-1,4-β-D-glucan 4-glucanohydrolase) gene in *Escherichia coli*", *Applied and Environmental Microbiology*, 54:2672–2676 (1988) and "DNA sequence of a *Fibrobacter succinogenes* mixed-linkage β-glucanase (1,3-1,4-β-D-glucan 4-glucanohydrolase) gene", *J. Bacteriology*, 172:3837–3841 (1990). Thus, it is believed unnecessary to further describe the process of cloning the glucanase gene herein.

The full-length cDNA of Fsβ-glucanase in a DNA template, such as the pJI10 plasmid as used in the preferred embodiment described herein, is amplified and introduced with a Nco I and an EcoR I restriction enzyme recognition sites at 5' and 3' ends, respectively, by using a PCR-based method. The two primers designed for introducing the Nco I and Eco RI sites are 5'TCACCACCATGGTTAGCG-CAAAG-3'(SEQ ID NO: 7), and 5'GCCACGAATTCTGT-TCAAAGTTC AC-3'(SEQ ID NO: 8), respectively. The PCR reaction is performed with a thermo-cycling program as follows: (94° C., 5 min; 55° C., 1 min, 72° C., 1 min for 1 cycle), (94° C., 1 min; 55° C., 1 min, 72° C., 1 min for 30 cycles), (94° C., 1.5 min; 55° C., 1.5 min, 72° C., 10 min for 1 cycle). The resulting amplified DNA fragments are digested with Nco I and Eco RI, purified, and ligated onto the pET26b (+) vector which is pre-digested with Nco I and Eco RI. The sequence of Fsβ-glucanase can be confirmed by any conventional DNA sequencing methods, such as the chain termination method (Sanger, 1977). In this DNA construct, a pel B leading peptide at the N-terminus and extra 19 amino acid residues including 6X-histidine tag at the C-terminus to facilitate protein purification are included. The recombinant plasmid encoding for the wild-type enzyme is then transformed into *E. coli* BL21 (DE3) host.

It is to be understood that the purpose of practice of the present invention, the wild-type glucanase may be obtained from sources other than pJI10 originated by Teather and Erfle (1988 & 1990). The wild-type gene from such other sources may vary in sequence in certain regions non-critical to the enzyme's function. Similarly, the truncated glucanase of the present invention may have varied sequences in regions not critical to the enzyme's function. Therefore, the present invention is not limited to the exact sequence as disclosed herein. As used in the claims annexed to this disclosure, the phrases "substantially identical" and "substantially corresponding" mean that the claims cover enzymes or DNA coding fragments that have minor sequence variations from the specified sequences that do not affect the enzyme's enzymatic functions to any significant degrees.

Gene Truncation

The gene for 1,3-1,4-β-D-glucanase (PCR-TF-glucanase) can be truncated by using a PCR method, which uses Oligo A and Oligo B as a pair of specific primers and the full length cDNA of Fsβ-glucanase in pJI10 as template. Oligo A: 5'-CAGCCGGCGATGGCCATGGTTAGCGCA-3' (SEQ ID NO: 9) and oligo B: 5'-CTGCTAGAAGAATTCGGAG-CAGGTTCGTC-3' (SEQ ID NO: 10), are designed to amplify both strands of the gene corresponding to the amino acid sequence from methionine 1 to proline 248. The amplified DNA fragments are digested with Nco I and Eco RI and then ligated with a pET26b (+) vector (purchased from Novagen, Wis., USA) which is pre-digested with Nco I and Eco RI, forming a recombinant plasmid containing a truncated Fsβ-glucanase gene. The truncated gene of Fsβ-glucanase in the recombinant plasmid can be confirmed by a chain termination DNA sequencing method (Sanger, 1977). In this DNA construct, a pel B leading peptide at the N-terminus and an extra 19 amino acid residues with a 6X-histidine tag at the C-terminus with respect to that of TF-glucanase sequence are included. Finally, the plasmid containing the truncated glucanase gene can then be transformed into *E. coli* BL21(DE3) host, purchased from Novagen, Wis., USA. Of course, other gene truncation methods or agents may be used satisfactorily.

In general, any method may be used if it can transfer or place a desired portion of Fsβ-glucanase gene in between an initiation codon and a stop codon of a expression frame of a suitable vector may be used.

Expression of Recombinant Glucanase Genes in *E. Coli*.

5 ml of pre-grown culture of the BL21 (DE3) bacterial strain carrying the pET26b (+) plasmid containing the Fsβ-glucanase gene or a truncated variation is added to 500 ml of fresh LB broth containing 30 μg/ml kanamycin. The culture is shaken vigorously at 33° C. until the OD reading at 600 nm reaches 0.4–0.6. Then, add 1 mM of IPTG to the culture and further incubate for 16 hour at 33° C. Under those culture conditions, the wild-type glucanase or truncated enzyme can be effectively expressed and secreted into the medium as a soluble protein. In general, same culture conditions can be used for expression of either full-length wild-type gene or a truncated gene. Of course, other variations of culture conditions are possible and the above stated parameters are merely provided as an example. For instance, the LB culture medium can be replaced with NZCYM or M9 medium and the incubation temperature can be varied within a wide range.

LB (pH7.0) contains: 1% (w/v) bacto-tryptone, 0.5% (w/v) bacto-yeast extract, and 1% (w/v) NaCl. NZCYM medium (pH 7.0) contains: 1% (w/v) NZ amine (Sigma Chemical Co., MO, USA), 0.5% (w/v) NaCl, 0.5% (w/v) bacto-yeast extract, 0.1% (w/v) casamino acids, and 0.2% (w/v) MgSO4(7H$_2$O). M9 contains: 1× M9 salt [1.28% (w/v) Na2HPO4(7H$_2$O), 0.3% (w/v) KH2PO4, 0.05% (w/v) NaCl, 0.1% (w/v) NH4Cl], and 0.4% glucose.

Purification of Glucanases in the Culture Medium.

The wild-type or truncated forms of 1,3-1,4-β-D-glucanases produced in the above-described procedure can be further purified. The culture at the end of the planned incubation is centrifuged at 8,000×g for 15 min at 4° C. The supernatant, containing approximately 80–85% of the expressed protein product, is collected and concentrated ten (10) times using a Pellicon Cassette concentrator (Millipore, Bedford, Mass.) with a 10,000 $M_r$ cut-off membrane. The concentrated culture supernatant is then dialyzed against 50 mM Tris-HCl buffer, pH 7.8 (buffer A) and loaded onto a Sepharose Q FF (Pharmacia, Sweden) column pre-equilibrated with the same buffer. 1,3-1,4-β-D-Glucanase proteins, either the wild-type or a truncated form of the enzyme, is collected from the eluants of the column eluted with a 0–1 M NaCl salt gradient in buffer A. A second Ni-NTA affinity column equilibrated with 50 mM sodium phosphate (pH 8.0), 0.3 M NaCl, and 10 mM imidazole buffer (buffer B) is then employed for further purification of the enzymes. From a 10–300 mM imidazole gradient eluant, homogeneous enzyme preparation can be obtained, as verified by SDS-polyacrylamide gel electrophoresis (SDS-PAGE) according to Laemmli (1970). Protein concentration is quantified as described by Bradford (1976) with bovine serum albumin (BSA) as the standard. It is to be understood, however, that the purification method forms no part of the invention, other purification techniques, either existing now or to be developed in future, can be satisfactorily used.

Example II

Enzyme Truncation at the Protein Level

The first step in truncating the glucanase at the protein level is to produce the full-length wild type enzyme, which is fully described in the preceding sections in Example I. In summary, E. coli host cells harboring the full length Fsβ-glucanase gene are cultured in either LB, NZCYM, or M9 medium under conditions suitable for cell growth and protein expression. (IPTG may be added at a certain point of the incubation to induce the gene transcription). The active enzyme in the culture medium is then collected (by centrifugation and recovering the supernatant) and concentrated to an appropriate volume on a Pellicon Cassette concentrator (Millipore, USA) with a 10,000 $M_r$ cut-off membrane. The enzyme in the supernatant accounts about 80–85% of total expressed enzyme, and the remaining 15–20% is found in the cell pellet.

After concentrating the culture supernatant, the second step is to conduct post-expression modification of the protein structure. As an example, such post-expression modification to produce shortened protein can be achieved by incubating the concentrated culture supernatant for a prolonged period of time under certain conditions. In a preferred embodiment, the supernatant is incubated for 10–14 days at a temperature within the range from 4° C. to 37° C. Although, it is possible to use the same prolonged incubation process to obtain the truncated enzyme from the cell pellet which contains about 15–20% of the total enzyme, it is a less efficient method. Other incubation conditions, however, may also produce satisfactory results. It is believed that a propyl endopeptidase known as protease II in E. coli (Kanatani et al., 1991) may play a major proteolytic role in the generation of TF-glucanase from the full-length enzyme.

Confirmation of the Improved Enzymatic Property

The following description imposes no limitations to the present invention, but merely serves to further characterize the above disclosed embodiments.

Structural Characterisation of Truncated Enzymes

Figure 2:
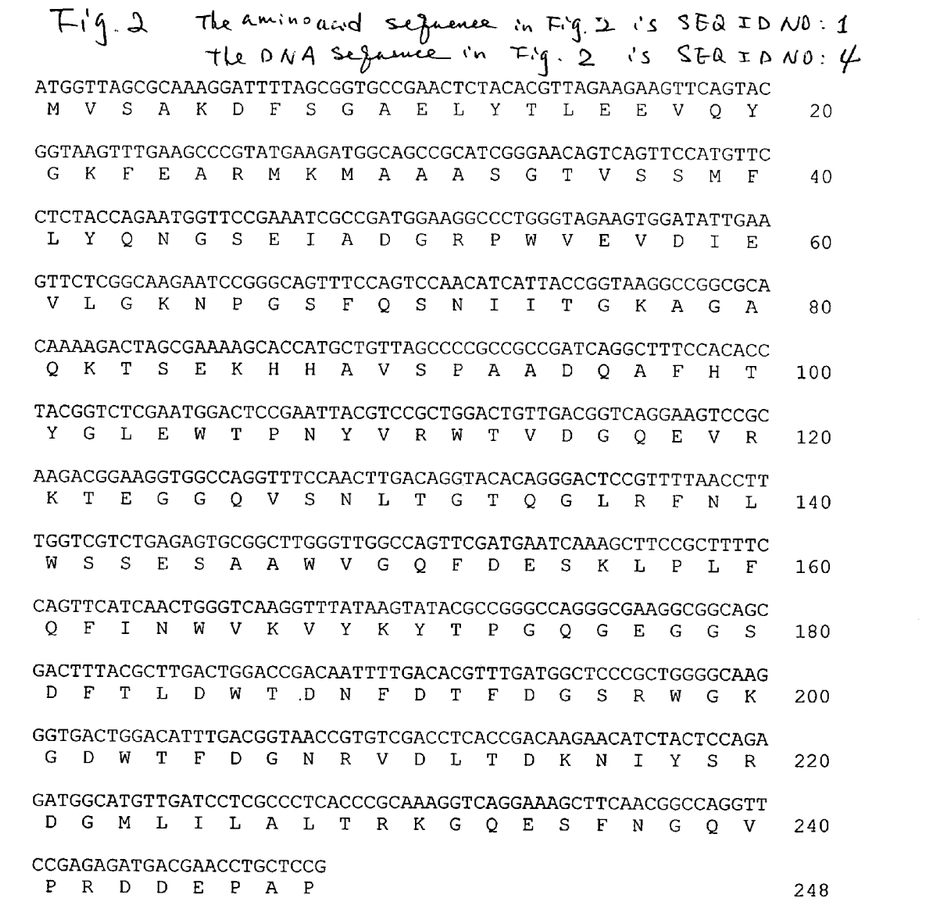
FIG. 2 is the amino acid sequence of TF-glucanase (SEQ ID NO: 1) as one embodiment of present invention, and its corresponding genetic nucleotide sequence (SEQ ID NO: 4).
Figure 3:
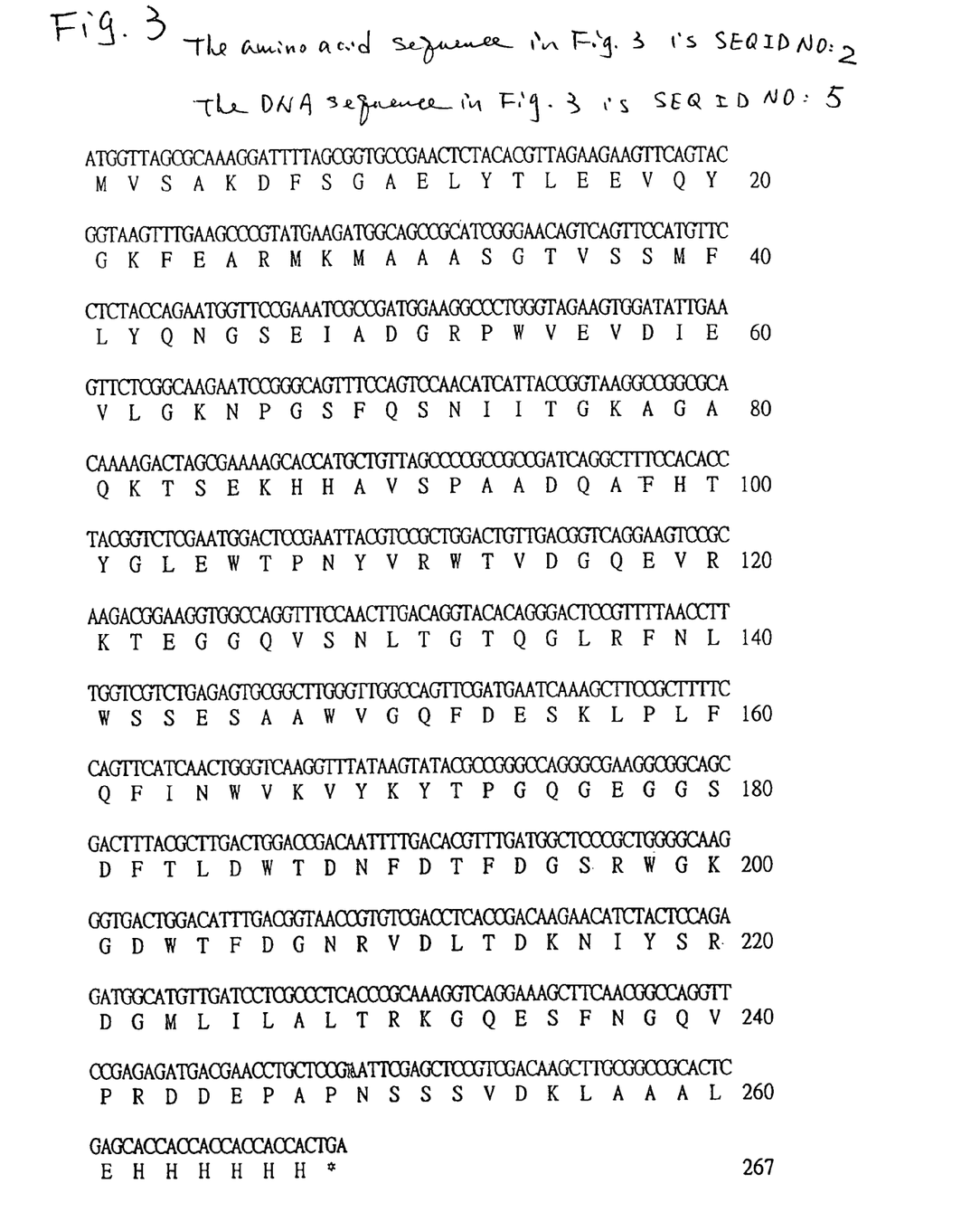
FIG. 3 is the amino acid sequence of PCR-TF-glucanase (SEQ ID NO: 2) as another embodiment of present invention, and its corresponding genetic nucleotide sequence (SEQ ID NO: 5).

The post-expression truncation of the wild-type enzyme produces a mixture of truncated enzyme molecules with a molecular weight ranging from 27 kDa to 37.5 kDa. However, there is a dominant species, referred as TF-glucanase, that has a molecular weight of approximately 27.7 kDa, that is, about 10 kDa smaller than that of the full-length enzyme. This dominant TF-glucanase is formed after 10 to 14 days post-expression incubation in the LB medium at 25° C., and is stable and active even if when the incubation time is extended for up to 45 days at 25° C. The sequence of this dominant TF-glucanase is presented in FIG. 2, which suggests that TF-glucanase is produced when approximately 80 amino acid residues are removed from the C-terminus of the wild-type enzyme. On the other hand, the PCR-generated truncated enzyme, i.e., PCR-TF-glucanase, has a molecular weight of 29.7 kDa, and shares the same amino acid sequence with TF-glucanase except that PCR-TF-glucanase has 19 extra amino acid residues at the C-terminus, see FIG. 3. Five P-X-S-S-S-S repeats and a basic terminal domain (BTD) located in the C-terminal portion of the wild-type enzyme (SEQ ID NO: 11) are absent from either TF-glucanase or PCR-TF-glucanase. The symbol P represents proline, S presents serine, and X represents an uncharged residue, such as alanine, proline, or glutamine.

Biochemical and Kinetic Characterization

Zymogram is used to measure enzymatic activity of various forms of glucanase, which is performed essentially according to a reported method (Piruzian et al., 1998). A 12% SDS polyacrylamide gel containing lichenan (1 mg/ml) and protein samples in sample buffer (Laemmli, 1970) pretreated at 90° C. for 10 min are prepared for the zymogram analysis. After electrophoresis, the gel is rinsed twice with 20% isopropanol in 50 mM sodium citrate buffer (pH 6.0) for 20 min to remove SDS, and then equilibrated in 50 mM sodium citrate buffer for 20 min. Before staining with Congo red solution (0.5 mg/ml), the gel is pre-incubated at 40° C. for 10 min. The protein bands with 1,3-1,4-β-D-glucanase activity can be visualized using the Congo red staining.

Figure 4:
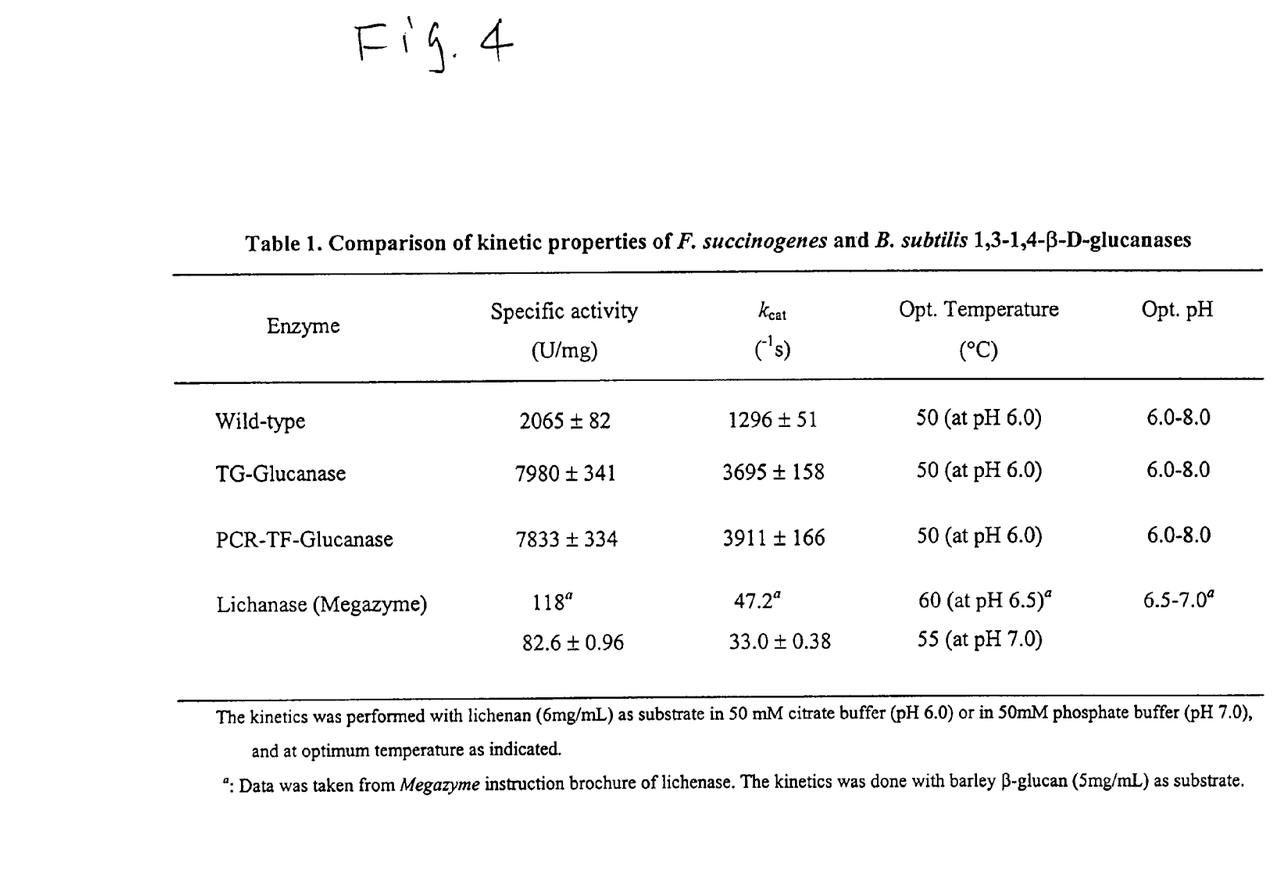
FIG. 4 is the kinetic data showing the truncated enzyme of the present invention has an enhanced enzymatic properties over the wild-type enzyme and a currently available commercial enzyme.

With reference to FIG. 4, experiments on kinetic studies are mainly performed using lichenan as the substrate. The specific activity of the wild-type (full length) Fsβ-glucanase, TF-glucanase, and PCR-TF-glucanase enzymes are 2065±82, 7980±341, and 7833±334 U/mg, respectively. Thus, a 3.9-fold increase in the specific activity is achieved in the truncated enzymes as compared with the wild-type enzyme. A slight decrease (1.5-fold) in the affinity for lichenan ($K_m$) is detected in the TF-glucanase and PCR-TF-glucanase relative to the wild-type enzyme. The turnover number ($k_{cat}$) and catalysis efficiency ($k_{cat}/K_m$) are 2 or 3-fold higher in the truncated enzymes than in the wild-type enzyme. The TF-glucanase is shown to have similar kinetic properties to those of PCR-TF-glucanase. The kinetic properties of the three forms of glucanase with barley β-glucan as substrate is also examined. The $V_{max}$ and $K_m$ values for wild-type, TF-glucanase, and PCR-TF-glucanase enzymes with barley β-glucan as substrate are 2643±77, 7682±38, and 7975±22 μmol/min/mg, and 2.93±0.18, 3.05±0.03, and 3.86±0.02 mg/ml, respectively. For wild-type and truncated enzymes, the optimum temperature is around 50° C. when assayed with 50 mM citrate buffer (pH 6.0). Truncated and wild-type enzymes also show a similar pH profile within the range from 4 to 10 with the optimum pH ranging from 6 to 8.

Figure 5:
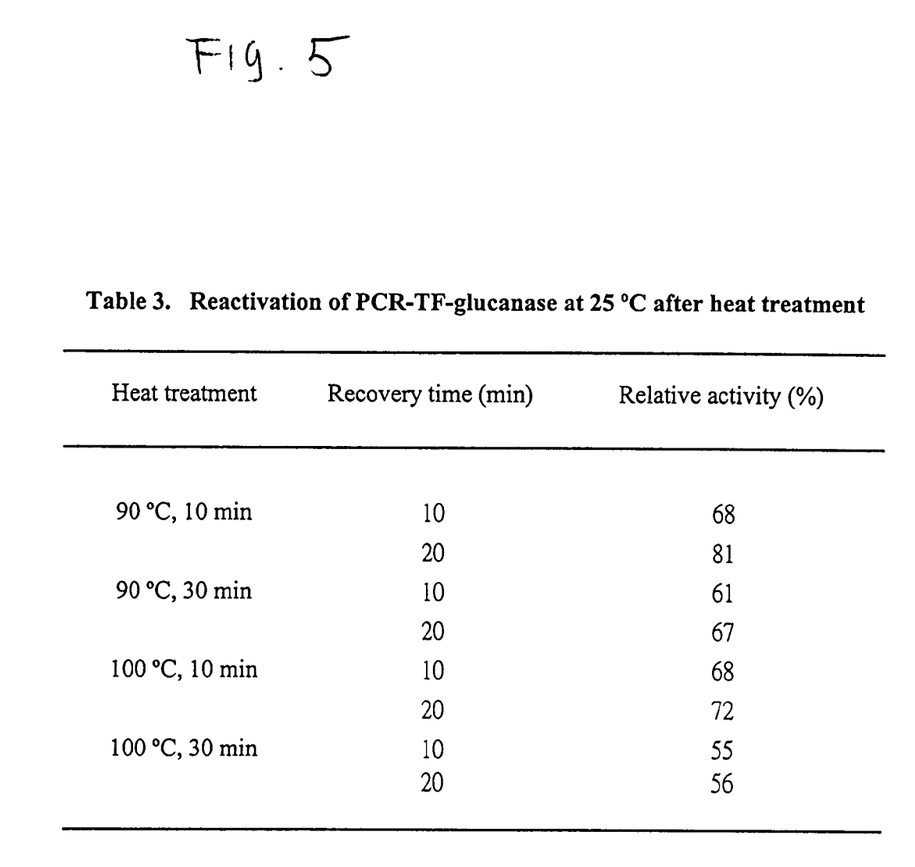
FIG. 5 is the data showing the truncated enzyme of the present invention possess a great thermal stability.
Figure 6:
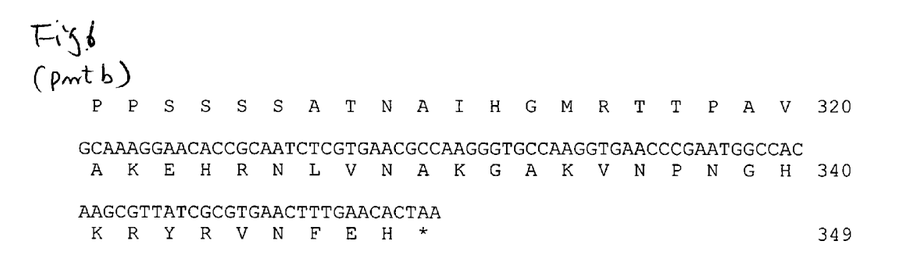
FIG. 6 is the amino acid sequence of the wild-type glucanase (SEQ ID NO: 3) as described by Teather and Erfle, and its corresponding genetic nucleotide sequence (SEQ ID NO: 6).

Recovery of enzymatic activity following a 10 minutes treatment at 90° C. is examined, see FIG. 5. The wild-type enzyme and PCR-TF-glucanase show 8% and 40%, respectively, of their original activity 3 minutes after transferring the heat-treated enzymes to room temperature. However, PCR-TF-glucanase recovers more than 80% of its original activity after be transferred to a 25° C. environment for 12 minutes while the recovery is 27% for the wild-type enzyme. Furthermore, the restored enzymatic activity of the wild-type enzyme is not stable and decreases to less than 10% of its original activity when incubated at 25° C. for four hours. In contrast, both PCR-TF-glucanase and TF-glucanase can maintain 70% of their original activity when incubated at 25° C. for 24 hour. PCR-TF-glucanase can recover 55 to 70% of its original activity after being boiled at about 100° C. for 10–30 minutes.

Lastly, the catalytic properties of a commercially available *Bacillus lichenase* from Megazyme Company are examined as a comparison to the truncated enzyme made according the present invention. The turnover rate ($k_{cat}$) of lichenase (Megazyme) is 47 s$^{-1}$ when using barley β-glucan as the substrate, and is 33 s$^{-1}$ with lichenan as the substrate, representing values 85-fold and 118-fold lower than those of PCR-TF-glucanase with respective substrates. Although the lichenase (Megazyme) has a higher optimum temperature (5–10° C. higher) than PCR-TF-glucanase, it is much less thermal stable. Enzymatic activity of the lichenase (Megazyme) can restored less than 10% of its original activity following a 90° C. heat treatment for 10 minute, whereas PCR-TF-glucanase, as mentioned above, readily recovers 80–85% of its original activity.

While there have been shown, described and pointed out the features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

The following list provides the sources of the references mentioned in the disclosure which may be helpful to people in the art to practice the present invention. The contents of all the listed publications are expressly incorporated into the disclosure by reference.

REFERENCES

1. Marilyn A. Anderson and B. A. Stone, "A NEW SUBSTRATE FOR INVESTIGATING THE SPECIFICITY OF β-GLUCAN HYDROLASES", North-holland Publishing Company—Amsterdam, vol. 52, no. 2, pp. 202–207, April 1975.
2. Bedford et al. "The effect of dietary enzyme supplementation of rye-and barely-based diets on digestion and subsequent performance in weanling pigs", Canadian Journal of Animal Science 72: pp. 95–105 (March 1992).
3. Marion M. Bradford, "A Rapid and Sensitive Method for the Quantitation of Microgram Quantities of Protein Utilizing the Principle of Protein-Dye Binding", Analytical Biochemistry 72, pp. 248–254 (1976).
4. Erfle et al. "Purification and properties of a 1,3-1,4-β-D-glucanase (lichenase, 1,3-1,4-β-D-glucan 4-glucanohydrolase, EC 3.2.1.73) from *Bacteriodes succinogenes* cloned in *Escherichia coli*, Biochem. J., vol. 225, pp. 833–841 (1988).
5. Hahn et al. "Native-like in vivo folding of a circularly permuted jellyroll protein shown by crystal structure analysis", Proc. Natl. Acad. Sci. USA, vol. 91, 10417–10421, October 1994.
6. Udo Heineman and Michael Hahn, "Circular permutations of protein sequence: not so rare?", TIBS 20 pp. 349–350, September 1995.
7. Keitel et al., "Molecular and active-site structure of a *Bacillus* 1,3-1,4-β-glucanase", Proc. Natl. Acad. Sci USA, vol. 90 pp. 5287–5291, June 1993.
8. U. K. Laemmli, "Cleavage of Structural Proteins during the Assembly of the Head of Bacteriophage T4", Nature Vol. 227, pp. 680–685, Aug. 15, 1970.
9. Maureen E. Louw and Sharon J. Reid, "Characterization, cloning and sequencing of a thermostable endo-(1,3-1,4) β-glucanase-encoding gene from an alkalophilic *bacillus brevis*", Applied Microbiology and Biotechnology, Springer-Vertag, vol. 38, pp. 507–513, (1993)
10. Gail Lorenz Miller, "Use of Dinitrosalicylic Acid Reagent for Determination of Reducing Sugar", Analytical Chemistry, vol. 31, no. 3, pp. 426–428, March 1959
11. Pirusian et al., "The use of thermostable β-glucanase gene from *Clostridium thermocellum* as a reporter gene in plants", Mol Gen Genet, vol. 257, pp. 561–567 (1998).
12. Politz et al., "Determinants for the enhanced thermostability of hybrid (1-3,14)-β-glucanases", Eur J. Biochem, vol. 216, pp. 829–834, (1993).
13. F. Sanger, "DNA sequencing with chain-terminating inhibitors", Pro. Natl. Acad. Sci. USA, vol. 74, No. 12, pp. 5463–5467, December 1977.
14. Silke Schimming, "Structure of the *Clostridium thermocellum* gene lic B and the encoded β-1,3-1,4-glucanase, Eur J. Biochem, vol. 204, pp. 13–19 (1992).
15. Selinger et al. "The Rumen: A Unique Source of Enzymes for Enhancing Livestock Production", Minister of Public Works and Government Services Canada, Anaerobe, vol., pp. 263–284, (1996).

16. Jean E. Irvin and Ronald M. Teather, "Cloning and Expression of a *Bacteroides* succinogenes Mixed-Linkage β-Glucanase (1,3-1,4-β-D-Glucan 4-Glucanohydrolase)Gene in *Escherichia coli*", Applied and Environmental Microbiology, vol. 54, no. 11, pp. 2672–2676, November 1988.

17. Ronald M. Teather and James D. Erfle, "DNA Sequence of a Fibrobacter succinogenes Mixed-Linkage β-Glucanase (1,3-1,4-β-Dglucan 4-Glucanohydrolase) Gene", Journal of Bacteriology, vol. 172, no. 7, pp. 3837–3841, July 1990.

18. Janda et al., "Enzymes in the Brewing Industry", Application of Technical Enzyme Preparations, pp. 254–271.

We claim:

1. An isolated truncated glucanase consisting of the amino acid sequence SEQ ID NO:1.

2. An isolated truncated glucanase consisting of the amino acid sequence SEQ ID NO:2.

* * * * *

```
                        SEQUENCE LISTING

<160> NUMBER OF SEQ ID NOS: 11

<210> SEQ ID NO 1
<211> LENGTH: 248
<212> TYPE: PRT
<213> ORGANISM: Artificial Sequence
<220> FEATURE:
<223> OTHER INFORMATION: Description of Artificial Sequence: Modified
      enzyme with enhanced activity and thermal stability

<400> SEQUENCE: 1

Met Val Ser Ala Lys Asp Phe Ser Gly Ala Glu Leu Tyr Thr Leu Glu
 1               5                  10                  15

Glu Val Gln Tyr Gly Lys Phe Glu Ala Arg Met Lys Met Ala Ala Ala
                20                  25                  30

Ser Gly Thr Val Ser Ser Met Phe Leu Tyr Gln Asn Gly Ser Glu Ile
            35                  40                  45

Ala Asp Gly Arg Pro Trp Val Glu Val Asp Ile Glu Val Leu Gly Lys
        50                  55                  60

Asn Pro Gly Ser Phe Gln Ser Asn Ile Ile Thr Gly Lys Ala Gly Ala
 65                 70                  75                  80

Gln Lys Thr Ser Glu Lys His His Ala Val Ser Pro Ala Ala Asp Gln
                85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
        115                 120                 125

Asn Leu Thr Gly Thr Gln Gly Leu Arg Phe Asn Leu Trp Ser Ser Glu
    130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
        195                 200                 205

Arg Val Asp Leu Thr Asp Lys Asn Ile Tyr Ser Arg Asp Gly Met Leu
    210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro
                245

<210> SEQ ID NO 2
<211> LENGTH: 267
<212> TYPE: PRT
<213> ORGANISM: Artificial Sequence
```

-continued

```
<220> FEATURE:
<223> OTHER INFORMATION: Description of Artificial Sequence: Modified
      enzyme with enhanced activity and thermal stability

<400> SEQUENCE: 2

Met Val Ser Ala Lys Asp Phe Ser Gly Ala Glu Leu Tyr Thr Leu Glu
  1               5                  10                  15

Glu Val Gln Tyr Gly Lys Phe Glu Ala Arg Met Lys Met Ala Ala Ala
             20                  25                  30

Ser Gly Thr Val Ser Ser Met Phe Leu Tyr Gln Asn Gly Ser Glu Ile
         35                  40                  45

Ala Asp Gly Arg Pro Trp Val Glu Val Asp Ile Glu Val Leu Gly Lys
 50                  55                  60

Asn Pro Gly Ser Phe Gln Ser Asn Ile Ile Thr Gly Lys Ala Gly Ala
 65                  70                  75                  80

Gln Lys Thr Ser Glu Lys His His Ala Val Ser Pro Ala Ala Asp Gln
             85                  90                  95

Ala Phe His Thr Tyr Gly Leu Glu Trp Thr Pro Asn Tyr Val Arg Trp
            100                 105                 110

Thr Val Asp Gly Gln Glu Val Arg Lys Thr Glu Gly Gly Gln Val Ser
            115                 120                 125

Asn Leu Thr Gly Thr Gln Gly Leu Arg Phe Asn Leu Trp Ser Ser Glu
130                 135                 140

Ser Ala Ala Trp Val Gly Gln Phe Asp Glu Ser Lys Leu Pro Leu Phe
145                 150                 155                 160

Gln Phe Ile Asn Trp Val Lys Val Tyr Lys Tyr Thr Pro Gly Gln Gly
                165                 170                 175

Glu Gly Gly Ser Asp Phe Thr Leu Asp Trp Thr Asp Asn Phe Asp Thr
            180                 185                 190

Phe Asp Gly Ser Arg Trp Gly Lys Gly Asp Trp Thr Phe Asp Gly Asn
                195                 200                 205

Arg Val Asp Leu Thr Asp Lys Asn Ile Tyr Ser Arg Asp Gly Met Leu
            210                 215                 220

Ile Leu Ala Leu Thr Arg Lys Gly Gln Glu Ser Phe Asn Gly Gln Val
225                 230                 235                 240

Pro Arg Asp Asp Glu Pro Ala Pro Asn Ser Ser Ser Val Asp Lys Leu
                245                 250                 255

Ala Ala Ala Leu Glu His His His His His His
            260                 265

<210> SEQ ID NO 3
<211> LENGTH: 349
<212> TYPE: PRT
<213> ORGANISM: Fibrobacter succinogenes

<400> SEQUENCE: 3

Met Asn Ile Lys Lys Thr Ala Val Lys Ser Ala Leu Ala Val Ala Ala
  1               5                  10                  15

Ala Ala Ala Ala Leu Thr Thr Asn Val Ser Ala Lys Asp Phe Ser Gly
             20                  25                  30

Ala Glu Leu Tyr Thr Leu Glu Glu Val Gln Tyr Gly Lys Phe Glu Ala
         35                  40                  45

Arg Met Lys Met Ala Ala Ala Ser Gly Thr Val Ser Ser Met Phe Leu
 50                  55                  60

Tyr Gln Asn Gly Ser Glu Ile Ala Asp Gly Arg Pro Trp Val Glu Val
 65                  70                  75                  80
```

-continued

```
Asp Ile Glu Val Leu Gly Lys Asn Pro Gly Ser Phe Gln Ser Asn Ile
            85                  90                  95
Ile Thr Gly Lys Ala Gly Ala Gln Lys Thr Ser Glu Lys His His Ala
        100                 105                 110
Val Ser Pro Ala Ala Asp Gln Ala Phe His Thr Tyr Gly Leu Glu Trp
    115                 120                 125
Thr Pro Asn Tyr Val Arg Trp Thr Val Asp Gly Gln Glu Val Arg Lys
130                 135                 140
Thr Glu Gly Gly Gln Val Ser Asn Leu Thr Gly Thr Gln Gly Leu Arg
145                 150                 155                 160
Phe Asn Leu Trp Ser Ser Glu Ser Ala Ala Trp Val Gly Gln Phe Asp
                165                 170                 175
Glu Ser Lys Leu Pro Leu Phe Gln Phe Ile Asn Trp Val Lys Val Tyr
            180                 185                 190
Lys Tyr Thr Pro Gly Gln Gly Glu Gly Gly Ser Asp Phe Thr Leu Asp
        195                 200                 205
Trp Thr Asp Asn Phe Asp Thr Phe Asp Gly Ser Arg Trp Gly Lys Gly
    210                 215                 220
Asp Trp Thr Phe Asp Gly Asn Arg Val Asp Leu Thr Asp Lys Asn Ile
225                 230                 235                 240
Tyr Ser Arg Asp Gly Met Leu Ile Leu Ala Leu Thr Arg Lys Gly Gln
                245                 250                 255
Glu Ser Phe Asn Gly Gln Val Pro Arg Asp Asp Glu Pro Ala Pro Gln
            260                 265                 270
Ser Ser Ser Ser Ala Pro Ala Ser Ser Ser Val Pro Ala Ser Ser
        275                 280                 285
Ser Ser Val Pro Ala Ser Ser Ser Ala Phe Val Pro Pro Ser Ser
    290                 295                 300
Ser Ser Ala Thr Asn Ala Ile His Gly Met Arg Thr Thr Pro Ala Val
305                 310                 315                 320
Ala Lys Glu His Arg Asn Leu Val Asn Ala Lys Gly Ala Lys Val Asn
                325                 330                 335
Pro Asn Gly His Lys Arg Tyr Arg Val Asn Phe Glu His
            340                 345
```

<210> SEQ ID NO 4
<211> LENGTH: 744
<212> TYPE: DNA
<213> ORGANISM: Artificial Sequence
<220> FEATURE:
<223> OTHER INFORMATION: Description of Artificial Sequence: DNA
      encoding a modified enzyme
<221> NAME/KEY: CDS
<222> LOCATION: (1)..(744)

<400> SEQUENCE: 4

```
atg gtt agc gca aag gat ttt agc ggt gcc gaa ctc tac acg tta gaa      48
Met Val Ser Ala Lys Asp Phe Ser Gly Ala Glu Leu Tyr Thr Leu Glu
  1               5                  10                  15 gaa gtt cag tac ggt aag ttt gaa gcc cgt atg aag atg gca gcc gca      96
Glu Val Gln Tyr Gly Lys Phe Glu Ala Arg Met Lys Met Ala Ala Ala
             20                  25                  30 tcg gga aca gtc agt tcc atg ttc ctc tac cag aat ggt tcc gaa atc     144
Ser Gly Thr Val Ser Ser Met Phe Leu Tyr Gln Asn Gly Ser Glu Ile
         35                  40                  45 gcc gat gga agg ccc tgg gta gaa gtg gat att gaa gtt ctc ggc aag     192
Ala Asp Gly Arg Pro Trp Val Glu Val Asp Ile Glu Val Leu Gly Lys
```

```
                50                  55                  60
aat ccg ggc agt ttc cag tcc aac atc att acc ggt aag gcc ggc gca       240
Asn Pro Gly Ser Phe Gln Ser Asn Ile Ile Thr Gly Lys Ala Gly Ala
 65                  70                  75                  80 caa aag act agc gaa aag cac cat gct gtt agc ccc gcc gcc gat cag       288
Gln Lys Thr Ser Glu Lys His His Ala Val Ser Pro Ala Ala Asp Gln
                 85                  90                  95 gct ttc cac acc tac ggt ctc gaa tgg act ccg aat tac gtc cgc tgg       336
Ala Phe His Thr Tyr Gly Leu Glu Trp Thr Pro Asn Tyr Val Arg Trp
            100                 105                 110 act gtt gac ggt cag gaa gtc cgc aag acg gaa ggt ggc cag gtt tcc       384
Thr Val Asp Gly Gln Glu Val Arg Lys Thr Glu Gly Gly Gln Val Ser
        115                 120                 125 aac ttg aca ggt aca cag gga ctc cgt ttt aac ctt tgg tcg tct gag       432
Asn Leu Thr Gly Thr Gln Gly Leu Arg Phe Asn Leu Trp Ser Ser Glu
    130                 135                 140 agt gcg gct tgg gtt ggc cag ttc gat gaa tca aag ctt ccg ctt ttc       480
Ser Ala Ala Trp Val Gly Gln Phe Asp Glu Ser Lys Leu Pro Leu Phe
145                 150                 155                 160 cag ttc atc aac tgg gtc aag gtt tat aag tat acg ccg ggc cag ggc       528
Gln Phe Ile Asn Trp Val Lys Val Tyr Lys Tyr Thr Pro Gly Gln Gly
                165                 170                 175 gaa ggc ggc agc gac ttt acg ctt gac tgg acc gac aat ttt gac acg       576
Glu Gly Gly Ser Asp Phe Thr Leu Asp Trp Thr Asp Asn Phe Asp Thr
            180                 185                 190 ttt gat ggc tcc cgc tgg ggc aag ggt gac tgg aca ttt gac ggt aac       624
Phe Asp Gly Ser Arg Trp Gly Lys Gly Asp Trp Thr Phe Asp Gly Asn
        195                 200                 205 cgt gtc gac ctc acc gac aag aac atc tac tcc aga gat ggc atg ttg       672
Arg Val Asp Leu Thr Asp Lys Asn Ile Tyr Ser Arg Asp Gly Met Leu
    210                 215                 220 atc ctc gcc ctc acc cgc aaa ggt cag gaa agc ttc aac ggc cag gtt       720
Ile Leu Ala Leu Thr Arg Lys Gly Gln Glu Ser Phe Asn Gly Gln Val
225                 230                 235                 240 ccg aga gat gac gaa cct gct ccg                                       744
Pro Arg Asp Asp Glu Pro Ala Pro
                245

<210> SEQ ID NO 5
<211> LENGTH: 804
<212> TYPE: DNA
<213> ORGANISM: Artificial Sequence
<220> FEATURE:
<223> OTHER INFORMATION: Description of Artificial Sequence: DNA
      encoding a modified enzyme
<221> NAME/KEY: CDS
<222> LOCATION: (1)..(804)

<400> SEQUENCE: 5 atg gtt agc gca aag gat ttt agc ggt gcc gaa ctc tac acg tta gaa        48
Met Val Ser Ala Lys Asp Phe Ser Gly Ala Glu Leu Tyr Thr Leu Glu
  1               5                  10                  15 gaa gtt cag tac ggt aag ttt gaa gcc cgt atg aag atg gca gcc gca        96
Glu Val Gln Tyr Gly Lys Phe Glu Ala Arg Met Lys Met Ala Ala Ala
                 20                  25                  30 tcg gga aca gtc agt tcc atg ttc ctc tac cag aat ggt tcc gaa atc       144
Ser Gly Thr Val Ser Ser Met Phe Leu Tyr Gln Asn Gly Ser Glu Ile
             35                  40                  45 gcc gat gga agg ccc tgg gta gaa gtg gat att gaa gtt ctc ggc aag       192
Ala Asp Gly Arg Pro Trp Val Glu Val Asp Ile Glu Val Leu Gly Lys
         50                  55                  60
```

-continued

```
aat ccg ggc agt ttc cag tcc aac atc att acc ggt aag gcc ggc gca      240
Asn Pro Gly Ser Phe Gln Ser Asn Ile Ile Thr Gly Lys Ala Gly Ala
 65                  70                  75                  80 caa aag act agc gaa aag cac cat gct gtt agc ccc gcc gcc gat cag      288
Gln Lys Thr Ser Glu Lys His His Ala Val Ser Pro Ala Ala Asp Gln
             85                  90                  95 gct ttc cac acc tac ggt ctc gaa tgg act ccg aat tac gtc cgc tgg      336
Ala Phe His Thr Tyr Gly Leu Glu Trp Thr Pro Asn Tyr Val Arg Trp
        100                 105                 110 act gtt gac ggt cag gaa gtc cgc aag acg gaa ggt ggc cag gtt tcc      384
Thr Val Asp Gly Gln Glu Val Arg Lys Thr Glu Gly Gly Gln Val Ser
    115                 120                 125 aac ttg aca ggt aca cag gga ctc cgt ttt aac ctt tgg tcg tct gag      432
Asn Leu Thr Gly Thr Gln Gly Leu Arg Phe Asn Leu Trp Ser Ser Glu
130                 135                 140 agt gcg gct tgg gtt ggc cag ttc gat gaa tca aag ctt ccg ctt ttc      480
Ser Ala Ala Trp Val Gly Gln Phe Asp Glu Ser Lys Leu Pro Leu Phe
145                 150                 155                 160 cag ttc atc aac tgg gtc aag gtt tat aag tat acg ccg ggc cag ggc      528
Gln Phe Ile Asn Trp Val Lys Val Tyr Lys Tyr Thr Pro Gly Gln Gly
                165                 170                 175 gaa ggc ggc agc gac ttt acg ctt gac tgg acc gac aat ttt gac acg      576
Glu Gly Gly Ser Asp Phe Thr Leu Asp Trp Thr Asp Asn Phe Asp Thr
            180                 185                 190 ttt gat ggc tcc cgc tgg ggc aag ggt gac tgg aca ttt gac ggt aac      624
Phe Asp Gly Ser Arg Trp Gly Lys Gly Asp Trp Thr Phe Asp Gly Asn
        195                 200                 205 cgt gtc gac ctc acc gac aag aac atc tac tcc aga gat ggc atg ttg      672
Arg Val Asp Leu Thr Asp Lys Asn Ile Tyr Ser Arg Asp Gly Met Leu
    210                 215                 220 atc ctc gcc ctc acc cgc aaa ggt cag gaa agc ttc aac ggc cag gtt      720
Ile Leu Ala Leu Thr Arg Lys Gly Gln Glu Ser Phe Asn Gly Gln Val
225                 230                 235                 240 ccg aga gat gac gaa cct gct ccg aat tcg agc tcc gtc gac aag ctt      768
Pro Arg Asp Asp Glu Pro Ala Pro Asn Ser Ser Ser Val Asp Lys Leu
                245                 250                 255 gcg gcc gca ctc gag cac cac cac cac cac cac tga                      804
Ala Ala Ala Leu Glu His His His His His His
            260                 265

<210> SEQ ID NO 6
<211> LENGTH: 1050
<212> TYPE: DNA
<213> ORGANISM: Fibrobacter succinogenes
<220> FEATURE:
<221> NAME/KEY: CDS
<222> LOCATION: (1)..(1047)

<400> SEQUENCE: 6 atg aac atc aag aaa act gca gtc aag agc gct ctc gcc gta gca gcc       48
Met Asn Ile Lys Lys Thr Ala Val Lys Ser Ala Leu Ala Val Ala Ala
  1               5                  10                  15 gca gca gca gcc ctc acc acc aat gtt agc gca aag gat ttt agc ggt       96
Ala Ala Ala Ala Leu Thr Thr Asn Val Ser Ala Lys Asp Phe Ser Gly
             20                  25                  30 gcc gaa ctc tac acg tta gaa gaa gtt cag tac ggt aag ttt gaa gcc      144
Ala Glu Leu Tyr Thr Leu Glu Glu Val Gln Tyr Gly Lys Phe Glu Ala
         35                  40                  45 cgt atg aag atg gca gcc gca tcg gga aca gtc agt tcc atg ttc ctc      192
Arg Met Lys Met Ala Ala Ala Ser Gly Thr Val Ser Ser Met Phe Leu
     50                  55                  60
```

```
tac cag aat ggt tcc gaa atc gcc gat gga agg ccc tgg gta gaa gtg      240
Tyr Gln Asn Gly Ser Glu Ile Ala Asp Gly Arg Pro Trp Val Glu Val
 65                  70                  75                  80 gat att gaa gtt ctc ggc aag aat ccg ggc agt ttc cag tcc aac atc      288
Asp Ile Glu Val Leu Gly Lys Asn Pro Gly Ser Phe Gln Ser Asn Ile
                 85                  90                  95 att acc ggt aag gcc ggc gca caa aag act agc gaa aag cac cat gct      336
Ile Thr Gly Lys Ala Gly Ala Gln Lys Thr Ser Glu Lys His His Ala
            100                 105                 110 gtt agc ccc gcc gcc gat cag gct ttc cac acc tac ggt ctc gaa tgg      384
Val Ser Pro Ala Ala Asp Gln Ala Phe His Thr Tyr Gly Leu Glu Trp
        115                 120                 125 act ccg aat tac gtc cgc tgg act gtt gac ggt cag gaa gtc cgc aag      432
Thr Pro Asn Tyr Val Arg Trp Thr Val Asp Gly Gln Glu Val Arg Lys
    130                 135                 140 acg gaa ggt ggc cag gtt tcc aac ttg aca ggt aca cag gga ctc cgt      480
Thr Glu Gly Gly Gln Val Ser Asn Leu Thr Gly Thr Gln Gly Leu Arg
145                 150                 155                 160 ttt aac ctt tgg tcg tct gag agt gcg gct tgg gtt ggc cag ttc gat      528
Phe Asn Leu Trp Ser Ser Glu Ser Ala Ala Trp Val Gly Gln Phe Asp
                165                 170                 175 gaa tca aag ctt ccg ctt ttc cag ttc atc aac tgg gtc aag gtt tat      576
Glu Ser Lys Leu Pro Leu Phe Gln Phe Ile Asn Trp Val Lys Val Tyr
            180                 185                 190 aag tat acg ccg ggc cag ggc gaa ggc ggc agc gac ttt acg ctt gac      624
Lys Tyr Thr Pro Gly Gln Gly Glu Gly Gly Ser Asp Phe Thr Leu Asp
        195                 200                 205 tgg acc gac aat ttt gac acg ttt gat ggc tcc cgc tgg ggc aag ggt      672
Trp Thr Asp Asn Phe Asp Thr Phe Asp Gly Ser Arg Trp Gly Lys Gly
    210                 215                 220 gac tgg aca ttt gac ggt aac cgt gtc gac ctc acc gac aag aac atc      720
Asp Trp Thr Phe Asp Gly Asn Arg Val Asp Leu Thr Asp Lys Asn Ile
225                 230                 235                 240 tac tcc aga gat ggc atg ttg atc ctc gcc ctc acc cgc aaa ggt cag      768
Tyr Ser Arg Asp Gly Met Leu Ile Leu Ala Leu Thr Arg Lys Gly Gln
                245                 250                 255 gaa agc ttc aac ggc cag gtt ccg aga gat gac gaa cct gct ccg caa      816
Glu Ser Phe Asn Gly Gln Val Pro Arg Asp Asp Glu Pro Ala Pro Gln
            260                 265                 270 tct tct agc agc gct ccg gca tct tct agc agt gtt ccg gca agc tcc      864
Ser Ser Ser Ser Ala Pro Ala Ser Ser Ser Ser Val Pro Ala Ser Ser
        275                 280                 285 tct agc gtc cct gcc tcc tcg agc agc gca ttt gtt ccg ccg agc tcc      912
Ser Ser Val Pro Ala Ser Ser Ser Ala Phe Val Pro Pro Ser Ser
    290                 295                 300 tcg agc gcc aca aac gca atc cac gga atg cgc aca act ccg gca gtt      960
Ser Ser Ala Thr Asn Ala Ile His Gly Met Arg Thr Thr Pro Ala Val
305                 310                 315                 320 gca aag gaa cac cgc aat ctc gtg aac gcc aag ggt gcc aag gtg aac     1008
Ala Lys Glu His Arg Asn Leu Val Asn Ala Lys Gly Ala Lys Val Asn
                325                 330                 335 ccg aat ggc cac aag cgt tat cgc gtg aac ttt gaa cac taa             1050
Pro Asn Gly His Lys Arg Tyr Arg Val Asn Phe Glu His
            340                 345
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

```
<400> SEQUENCE: 7
tcaccaccat ggttagcgca aag                                              23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
gccacgaatt ctgttcaaag ttcac                                            25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
cagccggcga tggccatggt tagcgca                                          27

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
ctgctagaag aattcggagc aggttcgtc                                        29

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      illustrative peptide
<221> NAME/KEY: MOD_RES
<222> LOCATION: (2)
<223> OTHER INFORMATION: An uncharged residue, such as Alanine, Proline
      or Glutamine

<400> SEQUENCE: 11

Pro Xaa Ser Ser Ser Ser
  1               5
```